US010413162B2

(12) United States Patent
Adachi

(10) Patent No.: US 10,413,162 B2
(45) Date of Patent: Sep. 17, 2019

(54) IMAGE SENSOR, ENDOSCOPE, AND ENDOSCOPE SYSTEM

(71) Applicant: OLYMPUS CORPORATION, Tokyo (JP)

(72) Inventor: Satoru Adachi, Tsuchiura (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/799,003

(22) Filed: Oct. 31, 2017

(65) Prior Publication Data

US 2018/0064314 A1 Mar. 8, 2018

Related U.S. Application Data

(63) Continuation of application No. PCT/JP2016/077293, filed on Sep. 15, 2016.

(30) Foreign Application Priority Data

Nov. 30, 2015 (JP) .................................. 2015-233554

(51) Int. Cl.
*A61B 1/00* (2006.01)
*A61B 1/04* (2006.01)
(Continued)

(52) U.S. Cl.
CPC ...... *A61B 1/00096* (2013.01); *A61B 1/00006* (2013.01); *A61B 1/00009* (2013.01);
(Continued)

(58) Field of Classification Search
CPC . A61B 1/00006; A61B 1/00009; A61B 1/041; A61B 1/045; A61B 1/051;
(Continued)

(56) References Cited

U.S. PATENT DOCUMENTS

2004/0201949 A1* 10/2004 Kida .................. H01G 9/012
361/306.1
2008/0012973 A1* 1/2008 Park .................. H04N 5/335
348/294

(Continued)

FOREIGN PATENT DOCUMENTS

EP 2 234 387 A1 9/2010
EP 3 258 492 A1 12/2017
(Continued)

OTHER PUBLICATIONS

International Search Report dated Nov. 29, 2016 issued in PCT/JP2016/077293.
(Continued)

*Primary Examiner* — Timothy J Neal
*Assistant Examiner* — William B Chou
(74) *Attorney, Agent, or Firm* — Scully, Scott, Murphy & Presser, P.C.

(57) ABSTRACT

An image sensor includes: a light reception unit; first transfer lines; a constant current source; second transfer lines; a reading unit; a control unit; a dielectric interposed between the first and second transfer lines formed in pairs; a first chip including at least the light reception unit, the plurality of first transfer lines, and the constant current source, each being mounted on the first chip; and a second chip including at least the second transfer lines mounted on the second chip. The first chip is configured such that the second chip is stacked on a back surface of a light receiving surface of the light reception unit, and each of the second transfer lines is arranged at a position facing one of the first transfer lines with the dielectric interposed between the first and second transfer lines.

6 Claims, 12 Drawing Sheets

(51) Int. Cl.
  *A61B 1/05*    (2006.01)
  *A61B 1/045*   (2006.01)
  *H01L 27/146*  (2006.01)
  *G02B 23/24*   (2006.01)
  *H04N 7/18*    (2006.01)
  *H04N 5/378*   (2011.01)
  *A61B 1/06*    (2006.01)
  *H04N 5/225*   (2006.01)

(52) U.S. Cl.
  CPC .............. *A61B 1/041* (2013.01); *A61B 1/045* (2013.01); *A61B 1/051* (2013.01); *G02B 23/2461* (2013.01); *H01L 27/1464* (2013.01); *H01L 27/14634* (2013.01); *H04N 5/378* (2013.01); *H04N 7/18* (2013.01); *A61B 1/042* (2013.01); *A61B 1/05* (2013.01); *A61B 1/0669* (2013.01); *G02B 23/2446* (2013.01); *G02B 23/2484* (2013.01); *H04N 2005/2255* (2013.01)

(58) Field of Classification Search
  CPC .............. G02B 23/24; G02B 23/2461; H01L 27/14634; H01L 27/1464; H04N 5/378; H04N 7/18; H01G 9/26; H01G 9/28; G09G 3/3258; G09G 2300/0852; G09G 2300/0876; G09G 2310/0251; G09G 2370/08; G02F 1/136213
  USPC ...... 600/109, 110, 112, 160; 348/45, 65, 69, 348/70, 76, 77, 294
  See application file for complete search history.

(56) References Cited

U.S. PATENT DOCUMENTS

| | | | |
|---|---|---|---|
| 2008/0266434 A1* | 10/2008 | Sugawa | H01L 27/14609 348/308 |
| 2011/0234830 A1* | 9/2011 | Kiyota | H01L 27/14609 348/222.1 |
| 2013/0025924 A1* | 1/2013 | Sasahara | H05K 3/301 174/260 |
| 2013/0107093 A1 | 5/2013 | Aoki | |
| 2013/0113060 A1 | 5/2013 | Matsunaga | |
| 2013/0181316 A1 | 7/2013 | Tsukimura et al. | |
| 2013/0264487 A1* | 10/2013 | Okada | G01T 1/16 250/393 |
| 2014/0048690 A1* | 2/2014 | Oshikubo | H04N 5/347 250/208.1 |
| 2014/0320618 A1* | 10/2014 | Akahane | H04N 5/363 348/65 |
| 2015/0029375 A1* | 1/2015 | Sugawa | H04N 5/3575 348/308 |
| 2015/0029376 A1 | 1/2015 | Sugawa et al. | |

FOREIGN PATENT DOCUMENTS

| | | |
|---|---|---|
| JP | H05268535 A | 10/1993 |
| JP | 2012019166 A | 1/2012 |
| JP | 2013098858 A | 5/2013 |
| JP | 2015156516 A | 8/2015 |
| WO | 2013157423 A1 | 10/2013 |

OTHER PUBLICATIONS

Extended Supplementary European Search Report dated Jul. 3, 2019 in European Patent Application No. 16 87 0262.9.

* cited by examiner

IMAGE SENSOR, ENDOSCOPE, AND ENDOSCOPE SYSTEM

CROSS-REFERENCE TO RELATED APPLICATION

This application is a continuation of PCT international application Ser. No. PCT/JP2016/077293 filed on Sep. 15, 2016 which designates the United States, incorporated herein by reference, and which claims the benefit of priority from Japanese Patent Applications No. 2015-233554, filed on Nov. 30, 2015, incorporated herein by reference.

BACKGROUND

The present disclosure relates to an image sensor, an endoscope, and an endoscope system.

In recent years, there is a known technique of reducing the chip area of a complementary metal oxide semiconductor (CMOS) image sensor by stacking a pixel chip including a photoelectric converter and a peripheral circuit chip constituting a controller and a signal processor as a peripheral circuit of the pixel chip (refer to JP 5-268535 A). A technique using a through-connection conductor (or through-silicon via (TSV)) is known as a means for electrically connecting between the stacked chips (refer to JP 2015-156516 A).

SUMMARY

An image sensor may include: a light reception unit arranged in a two-dimensional matrix and including a plurality of pixels configured to receive light from an outside and generate imaging signals corresponding to an amount of the received light; a plurality of first transfer lines arranged on a back surface of a light receiving surface of the light reception unit and each configured to transfer the imaging signals; a constant current source provided in each of the plurality of first transfer lines and configured to output the imaging signals from the pixel to the first transfer line; a plurality of second transfer lines each configured to form a capacitance in pairs with one of the plurality of first transfer lines and individually transfer the imaging signals output by the first transfer line; a reading unit configured to read the imaging signals transferred by the plurality of second transfer lines; a control unit configured to cause the reading unit to operate while the pixel is outputting the imaging signals; a dielectric interposed between the first and second transfer lines formed in pairs; a first chip including at least the light reception unit, the plurality of first transfer lines, and the constant current source, each being mounted on the first chip; and a second chip including at least the plurality of second transfer lines mounted on the second chip, wherein the first chip is configured such that the second chip is stacked on the back surface of the light receiving surface, and each of the plurality of second transfer lines is arranged at a position facing one of the plurality of first transfer lines with the dielectric interposed between the first and second transfer lines.

The above and other objects, features, advantages and technical and industrial significance of this disclosure will be better understood by reading the following detailed description of presently preferred embodiments of the disclosure, when considered in connection with the accompanying drawings.

DETAILED DESCRIPTION

Figure 1:
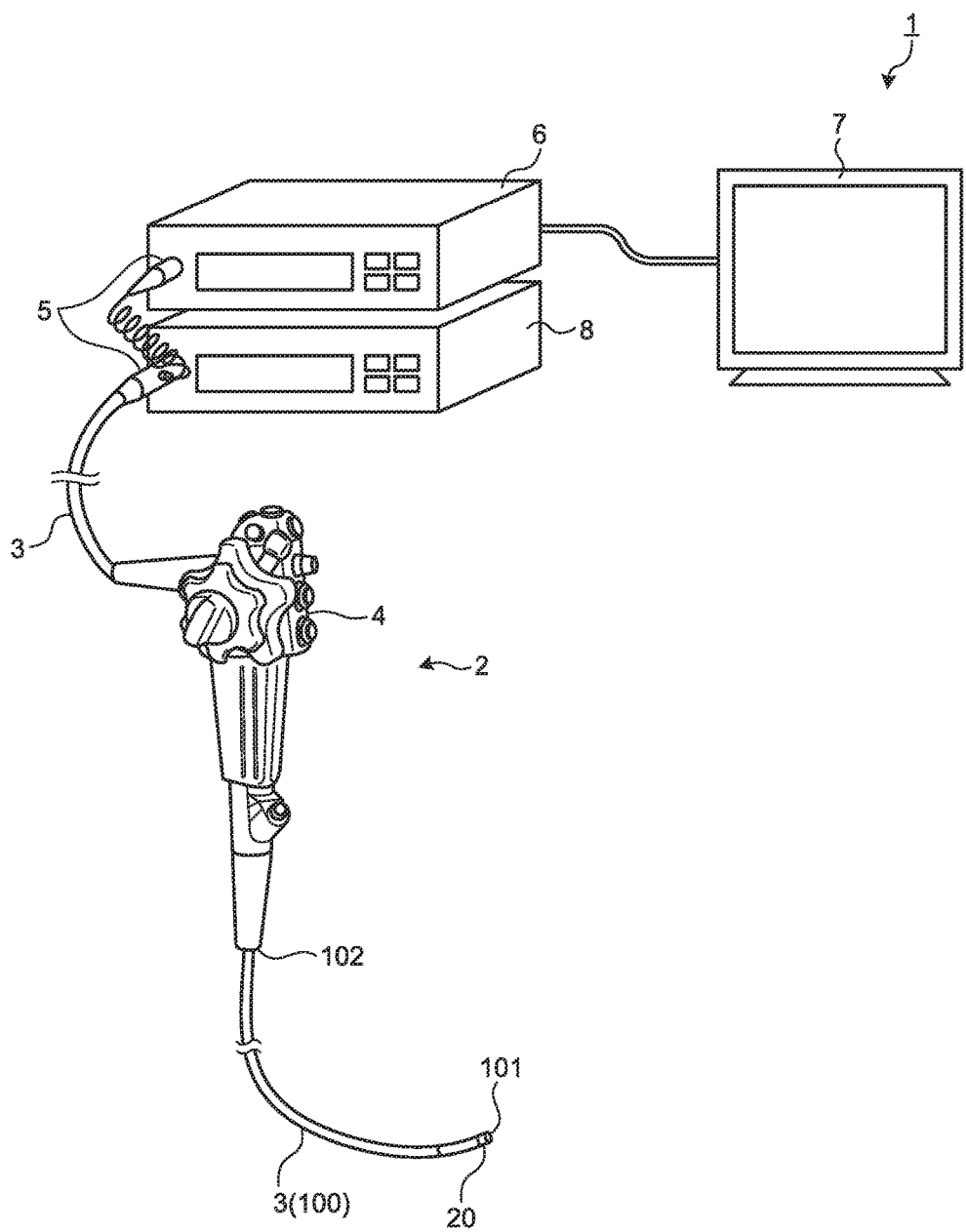
FIG. 1 is a diagram schematically illustrating an overall configuration of an endoscope system according to a first embodiment of the present disclosure.

Hereinafter, an endoscope system including an endoscope having a distal end to be inserted into a subject will be described according to embodiments (hereinafter, referred to as "embodiment(s)"). Note that the present disclosure is not intended to be limited by these embodiments. In the description of the drawings, the same portions are given the same reference numerals. Furthermore, it needs to be kept in mind that the drawings are schematic, and the relationship between the thickness and the width of individual members and the ratio between the members are different from an actual case. Still further, there are portions having different dimensions and ratios even between the drawings.

First Embodiment

Configuration of Endoscope System

FIG. 1 is a diagram schematically illustrating an overall configuration of an endoscope system according to a first embodiment. An endoscope system 1 illustrated in FIG. 1 includes an endoscope 2 (endoscope scope), a transmission cable 3, a connector unit 5, a processor 6 (processing apparatus), a display device 7, and a light source apparatus 8.

The endoscope 2 images the inside of the subject by inserting an insertion unit 100 being a portion of the transmission cable 3 into the body cavity of the subject, and outputs an imaging signal (image data) to the processor 6. The endoscope 2 includes an imaging unit 20 (image sensor) for capturing an in-vivo image at the one end side of the transmission cable 3, on a distal end 101 side of the insertion unit 100 to be inserted into the body cavity of the subject, and includes an operating unit 4 for receiving various types of operation onto the endoscope 2 on a proximal end 102 side of the insertion unit 100. An imaging signal of the image captured by the imaging unit 20 passes through the transmission cable 3 having a length of several meters, for example, and is output to the connector unit 5.

The transmission cable 3 connects the endoscope 2 with the connector unit 5 and connects the endoscope 2 with each of the processor 6 and the light source apparatus 8. Moreover, the transmission cable 3 propagates the imaging signal generated by the imaging unit 20 to the connector unit 5. The transmission cable 3 is constituted with a cable, an optical fiber, or the like.

The connector unit 5 is connected to the endoscope 2, the processor 6, and the light source apparatus 8, and performs predetermined signal processing on an imaging signal output from the connected endoscope 2, and together with this, converts an analog imaging signal into a digital imaging signal (A/D conversion) and outputs the converted signal to the processor 6.

The processor 6 performs predetermined image processing on the imaging signal input from the connector unit 5 and outputs the processed signal to the display device 7. The processor 6 totally controls the entire endoscope system 1. For example, the processor 6 performs control so as to switch illumination light emitted from the light source apparatus 8 and to switch imaging modes of the endoscope 2.

The display device 7 displays an image corresponding to the imaging signal on which the processor 6 has performed image processing. Moreover, the display device 7 displays various types of information related to the endoscope system 1. The display device 7 includes a display panel of liquid crystal, organic electroluminescence (EL), or the like.

The light source apparatus 8 emits illumination light from the distal end 101 side of the insertion unit 100 of the endoscope 2 toward a subject (object) via the connector unit 5 and the transmission cable 3. The light source apparatus 8 is constituted with a white light emitting diode (LED) which emits white light, or the like. Under the control of the processor 6, the light source apparatus 8 emits illumination light toward the subject via the endoscope 2. Note that while the light source apparatus 8 employs a simultaneous lighting method in the first embodiment, a sequential lighting method may also be employed.

Figure 2:
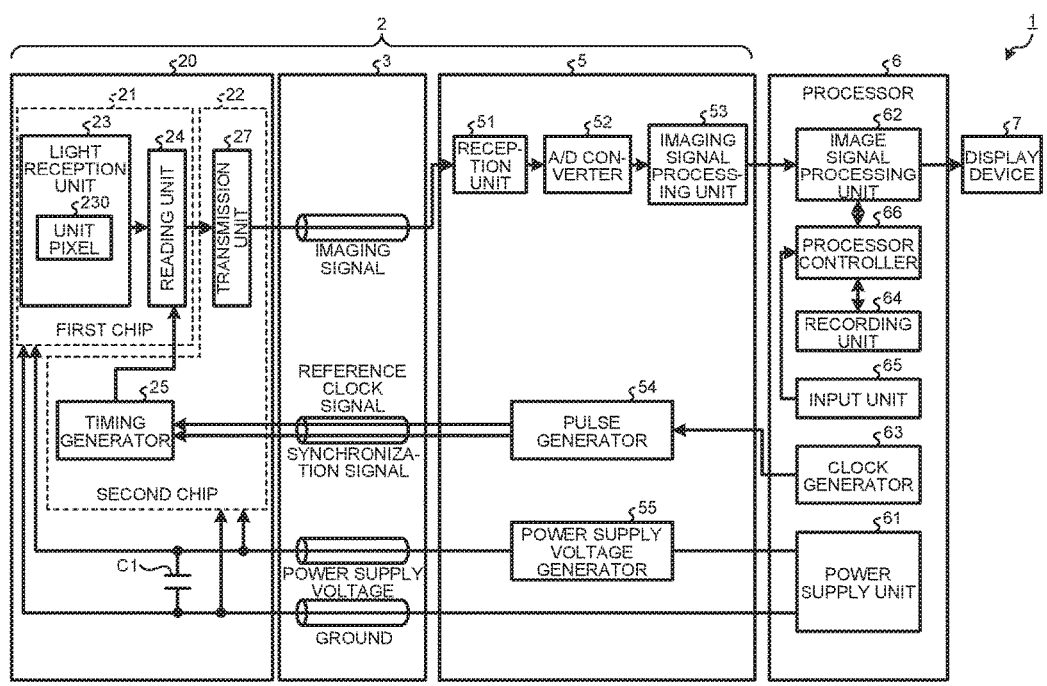
FIG. 2 is a block diagram illustrating a function of a main portion of the endoscope system according to the first embodiment of the present disclosure.

FIG. 2 is a block diagram illustrating a configuration of a main portion of the endoscope system 1. With reference to FIG. 2, details of a configuration of each of portions of the endoscope system 1 and electric signal paths in the endoscope system 1 will be described.

Configuration of Endoscope

First, a configuration of the endoscope 2 will be described. The endoscope 2 illustrated in FIG. 2 includes the imaging unit 20 (image sensor), the transmission cable 3, and the connector unit 5.

The imaging unit 20 includes a first chip 21 and a second chip 22. The imaging unit 20 receives a power supply voltage VDD generated by a power supply voltage generator 55 of the connector unit 5 described below via the transmission cable 3, together with the ground GND. A capacitance Cl for stabilizing the power supply is provided between the power supply voltage VDD and the ground GND supplied to the imaging unit 20.

The first chip 21 includes a light reception unit 23 and a reading unit 24. The light reception unit 23 is arranged in a two-dimensional matrix and has a plurality of unit pixels 230 configured to receive light from the outside and generate and output an imaging signal corresponding to the amount of received light, being arranged. The reading unit 24 reads an imaging signal photoelectrically converted by each of the plurality of unit pixels 230 in the light reception unit 23. A more detailed configuration of the first chip 21 will be described below.

The second chip 22 includes a timing generator 25 and a transmission unit 27. The timing generator 25 generates a timing signal on the basis of a reference clock signal and a synchronization signal input from the connector unit 5 and outputs the generated timing signal to the reading unit 24. The transmission unit 27 amplifies the imaging signal output from the reading unit 24 and outputs the amplified signal to the transmission cable 3. Combination of circuits arranged in the first chip 21 and the second chip 22 may be appropriately changed. For example, the timing generator 25 arranged in the second chip 22 may be arranged in the first chip 21. A more detailed configuration of the second chip 22 will be described below.

The connector unit 5 includes a reception unit 51, an A/D converter 52, an imaging signal processing unit 53, a pulse generator 54, and a power supply voltage generator 55.

The reception unit 51 receives an imaging signal output from the imaging unit 20, performs impedance matching using a passive element such as a resistor, then extracts an AC component using a capacitor and determines an operating point by a voltage dividing resistor. Thereafter, the reception unit 51 corrects the imaging signal (analog signal) and outputs the corrected signal to the A/D converter 52. The reception unit 51 is constituted with an analog front-end circuit, or the like.

The A/D converter 52 converts the analog imaging signal input from the reception unit 51 into a digital imaging signal and outputs the converted signal to the imaging signal processing unit 53.

The imaging signal processing unit 53 is constituted with a field programmable gate array (FPGA), or the like. The imaging signal processing unit 53 performs processing such as noise removal and format conversion processing on the digital imaging signal input from the A/D converter 52, and outputs the processed signal to the processor 6.

On the basis of a reference clock signal (for example, a clock signal of 27 MHz) supplied from the processor 6 and serving as a reference for operation of each of components of the endoscope 2, the pulse generator 54 generates a synchronization signal representing a start position of each of frames and outputs the signal to the timing generator 25 of the imaging unit 20 via the transmission cable 3, together with the reference clock signal. The synchronization signal generated by the pulse generator 54 includes a horizontal synchronization signal and a vertical synchronization signal.

The power supply voltage generator 55 generates a power supply voltage necessary for driving the first chip 21 and the second chip 22 from the power supply from the processor 6 and outputs the voltage to the first chip 21 and the second chip 22. The power supply voltage generator 55 generates the power supply voltage necessary for driving the first chip 21 and the second chip 22 using a regulator, or the like.

Configuration of Processor

Next, a configuration of the processor 6 will be described. The processor 6 is a control apparatus that totally controls the entire endoscope system 1. The processor 6 includes a power supply unit 61, an image signal processing unit 62, a clock generator 63, a recording unit 64, an input unit 65, and a processor controller 66.

The power supply unit 61 generates a power supply voltage and supplies the generated power supply voltage to the power supply voltage generator 55 of the connector unit 5 together with the ground (GND).

The image signal processing unit 62 performs image processing such as synchronization processing, white balance (WB) adjustment processing, gain adjustment processing, gamma correction processing, digital analog (D/A) conversion processing, and format conversion processing on the digital imaging signal that has undergone signal processing by the imaging signal processing unit 53, converts the processed signal into an image signal, and outputs the converted image signal to the display device 7.

The clock generator 63 generates a reference clock signal to be a reference for operation of each of the components of the endoscope system 1 and outputs the reference clock signal to the pulse generator 54.

The recording unit 64 records various types of information related to the endoscope system 1, data under processing, or the like. The recording unit 64 is constituted with a recording medium such as a flash memory and a random access memory (RAM).

The input unit 65 receives inputs of various types of operation related to the endoscope system 1. For example, the input unit 65 receives an input of an instruction signal for switching the type of illumination light emitted from the light source apparatus 8. The input unit 65 is constituted with a cross switch, a push button, or the like.

The processor controller 66 totally controls each of portions constituting the endoscope system 1. The processor controller 66 is constituted with a central processing unit (CPU), or the like. The processor controller 66 controls the endoscope system 1 in accordance with the instruction signal input from the input unit 65.

Detailed Configuration of Imaging Unit

Figure 3:
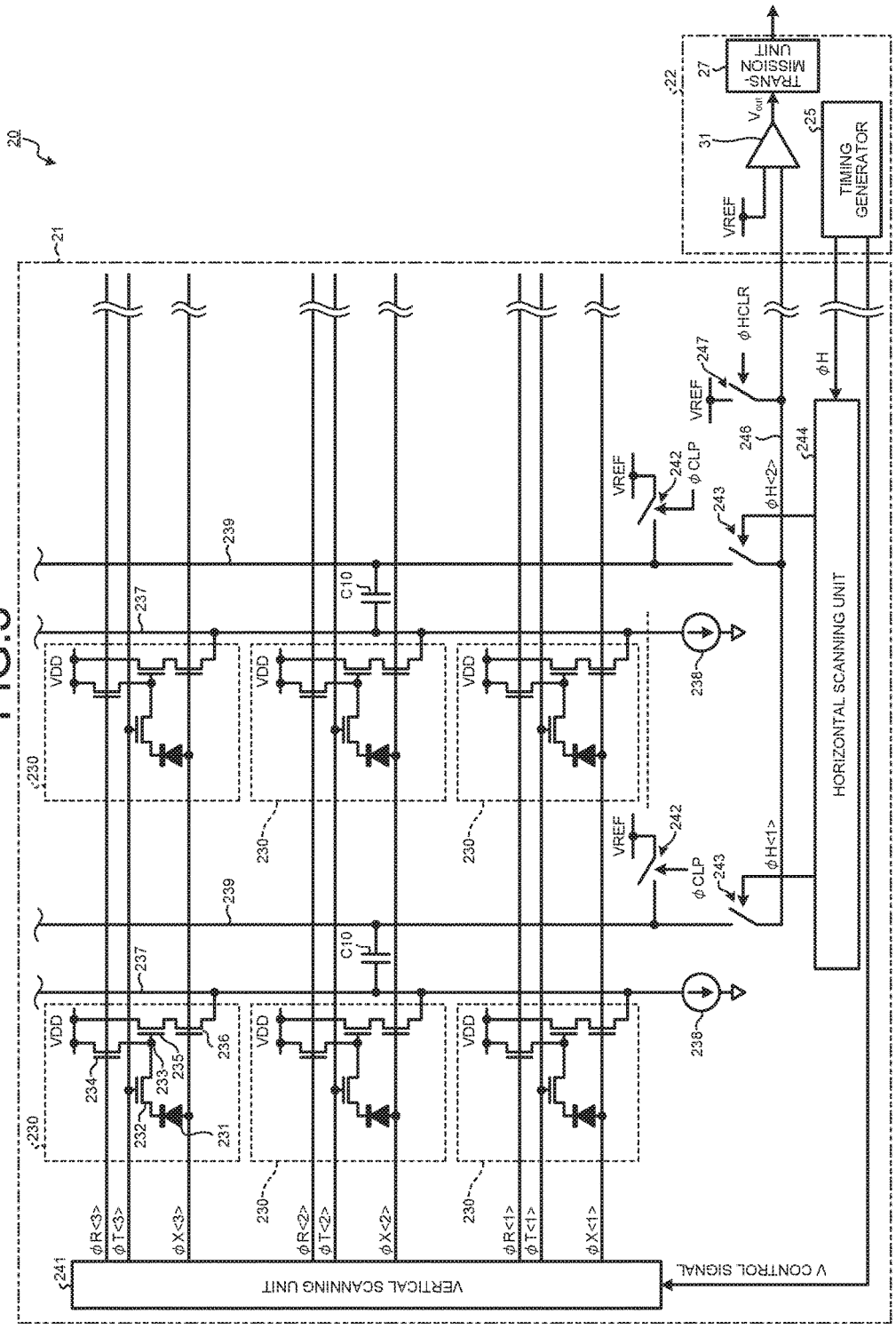
FIG. 3 is a block diagram illustrating a detailed configuration of an imaging unit illustrated in FIG. 2.

Next, detailed configurations of the first chip 21 and the second chip 22 in the above-described imaging unit 20 will be described. FIG. 3 is a block diagram illustrating a detailed configuration of the imaging unit 20 illustrated in FIG. 2.

Detailed Configuration of First Chip

First, a detailed configuration of the first chip 21 will be described.

As illustrated in FIG. 3, the first chip 21 includes the plurality of unit pixels 230 arranged in a two-dimensional matrix, a plurality of first transfer lines 237, and a constant current source 238 provided on each of the plurality of first transfer lines 237, a plurality of second transfer lines 239, a vertical scanning unit 241, a clamp unit 242, an output switch 243, a horizontal scanning unit 244, a third transfer line 246 (horizontal transfer line), and a horizontal reset unit 247.

Each of the unit pixels 230 includes a photoelectric conversion element 231 (photodiode), a transfer transistor 232 (first transfer portion), a charge-voltage converter 233, a charge-voltage converter reset unit 234 (transistor), a pixel source follower transistor 235, and a pixel output switch 236 (signal output unit).

The photoelectric conversion element 231 photoelectrically converts incident light into a signal charge amount corresponding to the amount of light and stores the amount. The cathode side of the photoelectric conversion element 231 is connected to one end side of the transfer transistor 232, and the anode side is connected to the ground GND.

The transfer transistor 232 transfers a charge from the photoelectric conversion element 231 to the charge-voltage converter 233. The transfer transistor 232 has one end side connected to the photoelectric conversion element 231, the other end side being connected to the charge-voltage converter 233, and has the gate connected to a signal line to which a drive pulse $\phi T$ <M> is supplied. When the drive pulse $\phi T$ <M> is supplied from the vertical scanning unit 241 described below via a signal line, the transfer transistor 232 is set to an on state and transfers the signal charge from the photoelectric conversion element 231 to the charge-voltage converter 233.

The charge-voltage converter 233 is formed with a floating diffusion (FD) capacitance, and converts the charge stored in the photoelectric conversion element 231 into a voltage.

The charge-voltage converter reset unit 234 resets the charge-voltage converter 233 to a predetermined potential. The charge-voltage converter reset unit 234 has one end side connected to the power supply voltage VDD, the other end side being connected to the charge-voltage converter 233, and has the gate connected to the signal line to which a drive pulse $\phi R$ <M> is supplied. When the drive pulse $\phi R$ <M> is supplied from the vertical scanning unit 241 described below via the signal line, the charge-voltage converter reset unit 234 is set to an on state and discharges the signal charge stored in the charge-voltage converter 233, and resets the charge-voltage converter 233 to a predetermined potential.

The pixel source follower transistor 235 has one end side connected to the power supply voltage VDD, the other end side being connected to the pixel output switch 236, and allows the gate to receive an input of a signal a signal charge-voltage converted by the charge-voltage converter 233 (imaging signal or signal at the time of reset).

The pixel output switch 236 outputs the signal charge-voltage converted by the charge-voltage converter 233 to the first transfer line 237 (first vertical transfer line) described below. The pixel output switch 236 has one end side connected to the pixel source follower transistor 235, the other end side being connected to the first transfer line 237, and has the gate connected to a signal line to which a row selection pulse $\phi X$ <M> is supplied. When the row selection pulse $\phi X$ <M> is supplied from the vertical scanning unit 241 described below via a signal line, the pixel output switch 236 is set to an on state, and transfers an imaging signal or a signal at the time of reset (noise signal) to the first transfer line 237.

The first transfer line 237 is arranged on the back surface of the light receiving surface and transfers the imaging signal output from the plurality of unit pixels 230. The first transfer line 237 is formed with metal wiring. Examples of the metal include Cu and Al.

The constant current source 238 has one end side connected to the ground GND and has the other end side connected to the first transfer line 237. The constant current source 238 is provided in each of the plurality of first transfer lines 237, and outputs an imaging signal from each of the plurality of unit pixels 230 to the first transfer line 237.

Each of the second transfer lines 239 forms a capacitance C10 in pairs with any one of the plurality of first transfer lines 237, and transfers the imaging signal output by the first transfer line 237. The capacitance C10 formed by each of the plurality of pairs of the first transfer line 237 and the second transfer line 239 is substantially equal to each other. Herein "substantially equal" is a range that may tolerate errors due to manufacturing variation. The second transfer line 239 is formed with metal wiring. Examples of the metal include Cu and Al.

On the basis of V control signals ($\phi X$, $\phi R$, $\phi T$, or the like) input from the timing generator 25, the vertical scanning unit 241 supplies each of the row selection pulse $\phi X$ <M>, the drive pulse φR <M>, and the drive pulse φT <M> to a selected row <M> (M=1, 2, . . . , m) of the light reception unit 23, thereby transferring the imaging signal and the noise signal at the time of reset from the unit pixels 230 driven by the constant current source 238 to the first transfer line 237 and the second transfer line 239.

The clamp unit 242 clamps a signal (noise signal) level at the time of reset of the unit pixel 230 transferred from the first transfer line 237 and the second transfer line 239, to a reference voltage VREF, and outputs the clamped signal to the output switch 243.

The output switch 243 has one end side connected to the second transfer line 239, the other end side being connected to the third transfer line 246, and allows the gate to receive an input of a column selection pulse φH <N> from the horizontal scanning unit 244. When the column selection pulse φH <N> is supplied to the gate, the output switch 243 is set to an on state, and transfers the difference between the voltage clamped by the clamp unit 242 and the signal transferred from the second transfer line 239 to the third transfer line 246, as an imaging signal.

On the basis of a drive pulse (φH) supplied from the timing generator 25, the horizontal scanning unit 244 supplies the column selection pulse φH <N> to the selected row <N> (N=1, 2, 3, . . . , n) of the light reception unit 23. By supplying the column selection pulse φH <N>, the horizontal scanning unit 244 allows the imaging signal from each of the unit pixels 230 to be output to the third transfer line 246.

The third transfer line 246 transfers the imaging signal output from each of the output switches 243 to an output unit 31.

The horizontal reset unit 247 resets the third transfer line 246 on the basis of a horizontal reset pulse φHCLR input from the timing generator 25. The horizontal reset unit 247 has one end side connected to the signal line that supplies the reference voltage VREF, the other end being connected to the third transfer line 246, and has the gate connected to the signal line to which the horizontal reset pulse φHCLR is supplied from the timing generator 25. In the first embodiment, each of the vertical scanning unit 241, the clamp unit 242, the output switch 243, the horizontal scanning unit 244, and the third transfer line 246 functions as the reading unit 24.

Detailed Configuration of the Second Chip

Next, a configuration of the second chip 22 will be described.

As illustrated in FIG. 3, the second chip 22 includes the timing generator 25, the transmission unit 27, and the output unit 31.

The timing generator 25 generates various drive pulses (V control signals, φHCLR, φCLP, φH) on the basis of the reference clock signal and the synchronization signal, and outputs each of the generated drive pulses to each of the vertical scanning unit 241, the clamp unit 242 and the horizontal scanning unit 244, respectively. In the first embodiment, the timing generator 25 functions as a control to cause the horizontal scanning unit 244 to operate while allowing the unit pixel 230 to output the imaging signal.

The transmission unit 27 amplifies the imaging signal transferred from the third transfer line 246 and transmits the amplified signal to the outside via the output unit 31.

The output unit 31 is constituted with a differential amplifier, and by obtaining the difference between the imaging signal transferred from the third transfer line 246 and the reference voltage VREF, outputs the imaging signal (Vout) from which the noise has been removed to the transmission unit 27.

Structure of First Chip

Next, a structure of the first chip 21 will be described.

Figure 4:
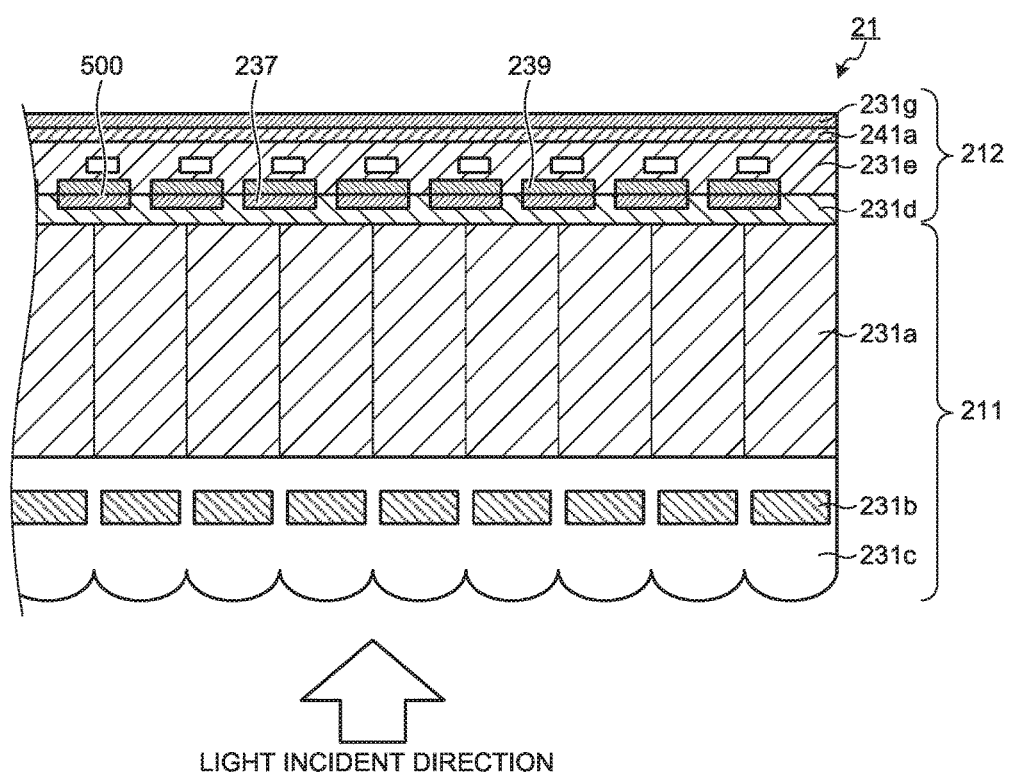
FIG. 4 is a diagram illustrating a cross-sectional structure of a light reception unit of a first chip according to the first embodiment of the present disclosure.

FIG. 4 is a diagram illustrating a cross-sectional structure of the light reception unit 23 of the first chip 21. As illustrated in FIG. 4, the light reception unit 23 of the first chip 21 includes a photoelectric conversion region portion 211 and a signal transfer region portion 212.

The photoelectric conversion region portion 211 is formed by stacking an on-chip color filter 231b and an on-chip microlens 231c in this order on the front surface side (light incident direction) of a silicon substrate 231a (light reception unit). Moreover, an interlayer insulating film 231d is stacked on the back side of the photoelectric conversion region portion 211, and the first transfer line 237 is formed in the interlayer insulating film 231d.

The signal transfer region portion 212 is stacked and formed on the back side of the photoelectric conversion region portion 211 as a portion of the reading unit 24 and is constituted with the second transfer line 239, an interlayer insulating film 231e, pixel drive wiring 241a, and a passivation film 231g.

The first transfer line 237 and the second transfer line 239 formed in pairs are arranged in parallel along a depth direction of FIG. 4. By arranging each of the second transfer lines 239 in pairs with any of the plurality of first transfer lines 237 via a dielectric 500 (dielectric film), the capacitance C10 is formed, whereby the imaging signal output from the first transfer line 237 is transferred to the second transfer line 239 as an input node of each of the reading units 24 (not illustrated). The second transfer line 239 and the reading unit 24 are connected with each other by a via hole, or the like. With this configuration, it is possible to stack the capacitance, which used to occupy the conventional column circuit area, on the back side of the first chip 21 in a direction orthogonal to the light receiving surface of the first chip 21 (light incidence direction), leading to reduction of the area of the imaging unit 20 including the first chip 21. Furthermore, the imaging unit 20 may enhance quantum efficiency by allowing light to be incident from a side opposite to a capacitance formation surface.

Structure of Capacitance

Next, a detailed structure of the capacitance C10 described in FIG. 4 will be described.

Figure 5:
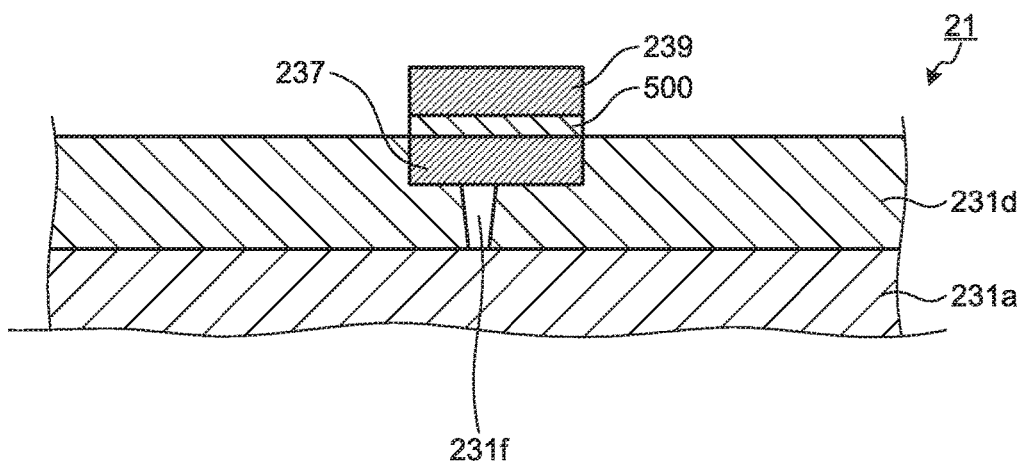
FIG. 5 is a diagram illustrating a cross-sectional structure of a capacitance of the first chip according to the first embodiment of the present disclosure.

FIG. 5 is a diagram illustrating a cross-sectional structure of the capacitance C10 of the first chip 21. The first chip 21 illustrated in FIG. 5 includes a contact hole 231f connecting a source region of the pixel output switch 236 formed on the silicon substrate 231a with the first transfer line 237. The first chip 21 further includes the dielectric 500 interposed between the first transfer line 237 and the second transfer line 239. The dielectric 500 is formed of, for example, $SiO_2$, $Si_3N_4$, $Al_2O_3$, $HfO_2$, $ZO_2$, $TaO_5$, $TiO_2$, $Y_2O_3$, and $La_2O_3$. This arrangement results in formation of the capacitance C10 between the first transfer line 237 and the second transfer line 239 formed in pairs, with the dielectric 500 being arranged between the metal wiring constituting each of the transfer lines.

Operation of Imaging Unit

Next, operation of the imaging unit 20 will be described.

Figure 6:
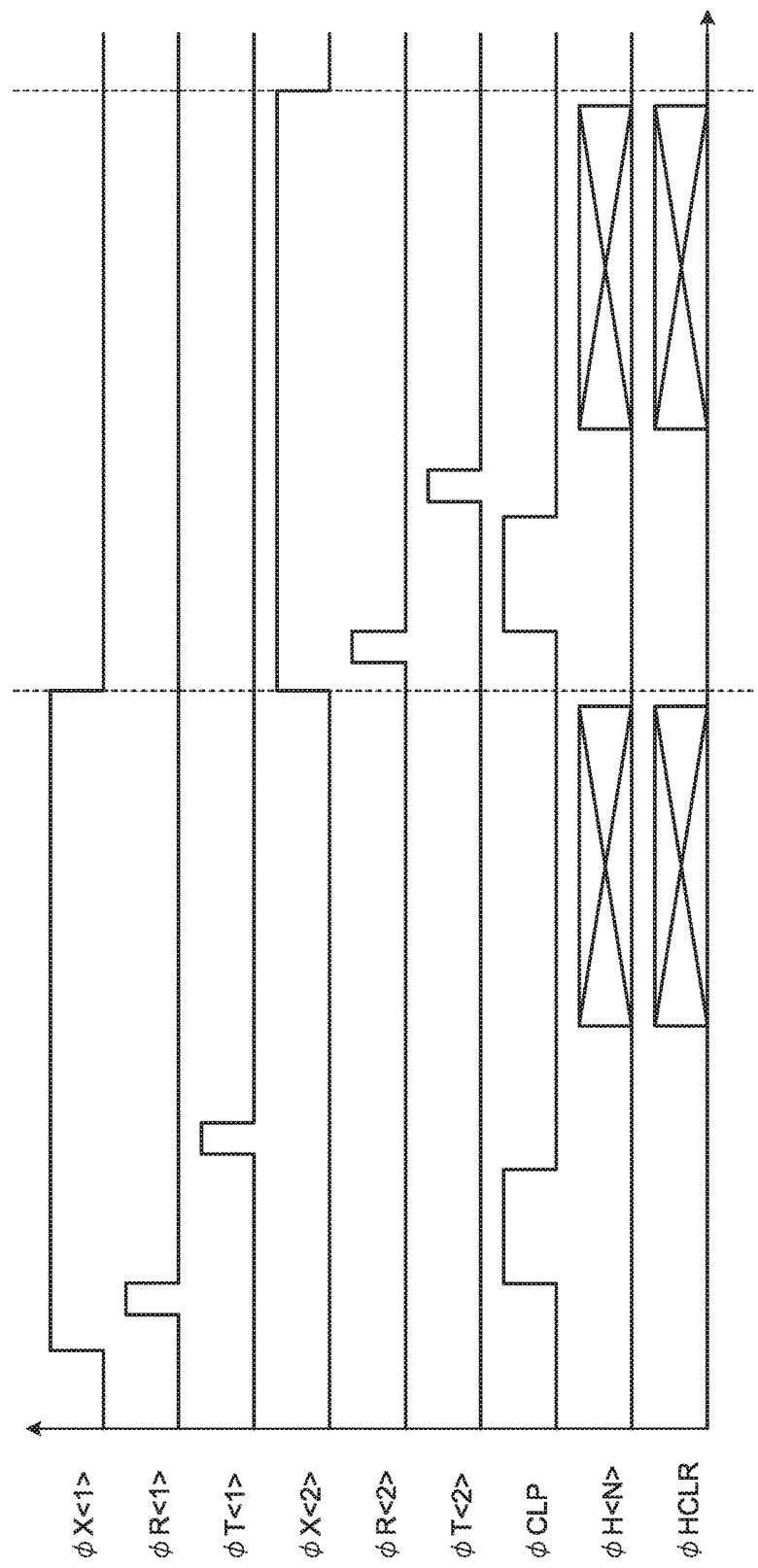
FIG. 6 is a timing chart illustrating an operation timing of the imaging unit according to the first embodiment of the present disclosure.

FIG. 6 is a timing chart illustrating an operation timing of the imaging unit 20. FIG. 6 illustrates, in order from the topmost stage, timings of the row selection pulse φX <1>, the drive pulse φR <1>, the drive pulse φT <1>, the drive pulse φCLP, the column selection pulse φH <N> (N=1, 2, 3, . . . , n), the row selection pulse φX <2>, the drive pulse φR <2>, the drive pulse φT <2>, the drive pulse φCLP, the column selection pulse φH <N> (N=1, 2, 3, . . . , n) and the horizontal reset pulse φHCLR. In FIG. 6, the horizontal axis represents time.

As illustrated in FIG. 6, the timing generator 25 first sets the drive pulse φR <1> to an on state while keeping the row selection pulse φX <1> to be set to the on state (High). This sets the charge-voltage converter reset unit 234 of the first row to an on state and allows the signal charge stored in the charge-voltage converter 233 of the first row to be discharged, and then, the charge-voltage converter 233 of the first row is reset to a predetermined potential.

Subsequently, the timing generator 25 sets the drive pulse φR <1> to an off state (Low) and sets the drive pulse φCLP to an on state. With this operation, the noise signal transferred from the first transfer line 237 is clamped to the reference voltage VREF by the clamp unit 242. That is, it is possible to reset the second transfer line 239 to a predetermined potential while the unit pixel 230 is outputting a reset level (noise signal).

Thereafter, the timing generator 25 sets the drive pulse φCLP to an off state (Low) and sets the drive pulse φT <1> to an on state (High), and thereafter sets it to an off state (Low). In this case, the transfer transistor 232 in the first row is set to an on state by inputting the drive pulse φT <1> into the gate, and the signal charge (imaging signal) is transferred from the photoelectric conversion element 231 to the charge-voltage converter 233.

Subsequently, the timing generator 25 exclusively sets the horizontal reset pulse φHCLR to an on/off state (High and Low) in accordance with the on/off operation of the column selection pulse φH while setting the column selection pulse φH <N> to an on/off state (High and Low) for each of the columns. In this case, in accordance with the on/off state of the column selection pulse φH <N>, the pixel output switch 236 in the first row of each of the columns sequentially outputs the imaging signal that has been charge-voltage converted by the charge-voltage converter 233, from the pixel source follower transistor 235 to the third transfer line 246 via the first transfer line 237 and the second transfer line 239. At this time, the horizontal reset unit 247 resets the third transfer line 246 to a predetermined potential (VREF) in accordance with the on/off state of the horizontal reset pulse φHCLR. With this sequence, a column circuit including a capacity for sampling the imaging signal may be omitted from the first chip 21, leading to achievement of miniaturization of the imaging unit 20.

Thereafter, the timing generator 25 sets the row selection pulse φX <1> to an off state (Low) and sets the row selection pulse φX <2> to an on state (High).

Subsequently, the timing generator 25 sets the drive pulse φR <2> to an on state while keeping the row selection pulse φX <2> in the on state (High). This sets the charge-voltage converter reset unit 234 of the second row to an on state and allows the signal charge stored in the charge-voltage converter 233 of the second row to be discharged, and then, the charge-voltage converter 233 of the second row is reset to a predetermined potential.

Subsequently, the timing generator 25 sets the drive pulse φR <2> to an off state (Low) and sets the drive pulse φCLP to an on state. With this operation, the noise signal transferred from the first transfer line 237 is clamped to the reference voltage VREF by the clamp unit 242. That is, it is possible to reset the second transfer line 239 to a predetermined potential while the unit pixel 230 is outputting a reset level (noise signal).

Thereafter, the timing generator 25 sets the drive pulse φCLP to an off state (Low) and sets the drive pulse φT <2> to an on state (High) and an off state (Low). In this case, the transfer transistor 232 in the second row is set to an on state by inputting the drive pulse φT <2> to the gate, and the signal charge (imaging signal) is transferred from the photoelectric conversion element 231 to the charge-voltage converter 233.

Subsequently, the timing generator 25 exclusively sets the horizontal reset pulse φHCLR to an on/off state (High and Low) in accordance with the on/off operation of the column selection pulse φH <N> while setting the column selection pulse φH <N> to an on/off state (High and Low) for each of the columns. In this case, in accordance with the on/off state of the column selection pulse φH <N>, the pixel source follower transistor 235 sequentially outputs, through the pixel output switch 236 in a second row of each of the columns, the imaging signal that has been charge-voltage converted by the charge-voltage converter 233 to the third transfer line 246 via the first transfer line 237 and the second transfer line 239. At this time, the horizontal reset unit 247 resets the third transfer line 246 to a predetermined potential (VREF) in accordance with the on/off state of the horizontal reset pulse φHCLR.

According to the first embodiment described above, the timing generator 25 causes the reading unit 24 to operate and output the imaging signal to the transmission unit 27 while allowing the unit pixel 230 to output the imaging signal. With this sequence, a column circuit including a capacity for sampling the imaging signal may be omitted from the first chip 21, leading to achievement of miniaturization of the imaging unit 20.

Moreover, according to the first embodiment, the capacitance formed by each of the plurality of pairs of the first transfer line 237 and the second transfer line 239 are substantially equal to each other, making it possible to suppress gain variation in individual columns due to capacitive division with the parasitic capacitance of the third transfer line 246. This leads to achievement of reduction of the area ratio of the peripheral circuit of the first chip 21 without causing image quality degradation due to fixed pattern noise such as longitudinal scratches.

Modification of First Embodiment

Next, a modification of the first embodiment will be described. The modification of the first embodiment is different in the configuration of the first chip. Specifically, in the modification of the first embodiment, a buffer unit is provided between the second transfer line 239 and the output switch 243, and an imaging signal transferred from the second transfer line 239 is amplified and output to the third transfer line 246. Hereinafter, a configuration of the first chip of the imaging unit according to the modification of the first embodiment will be described. A same reference sign will be given to the configuration identical to the configuration of the endoscope system 1 according to the above-described first embodiment, and description therefor will be omitted.

Detailed Configuration of Imaging Unit

Figure 7:
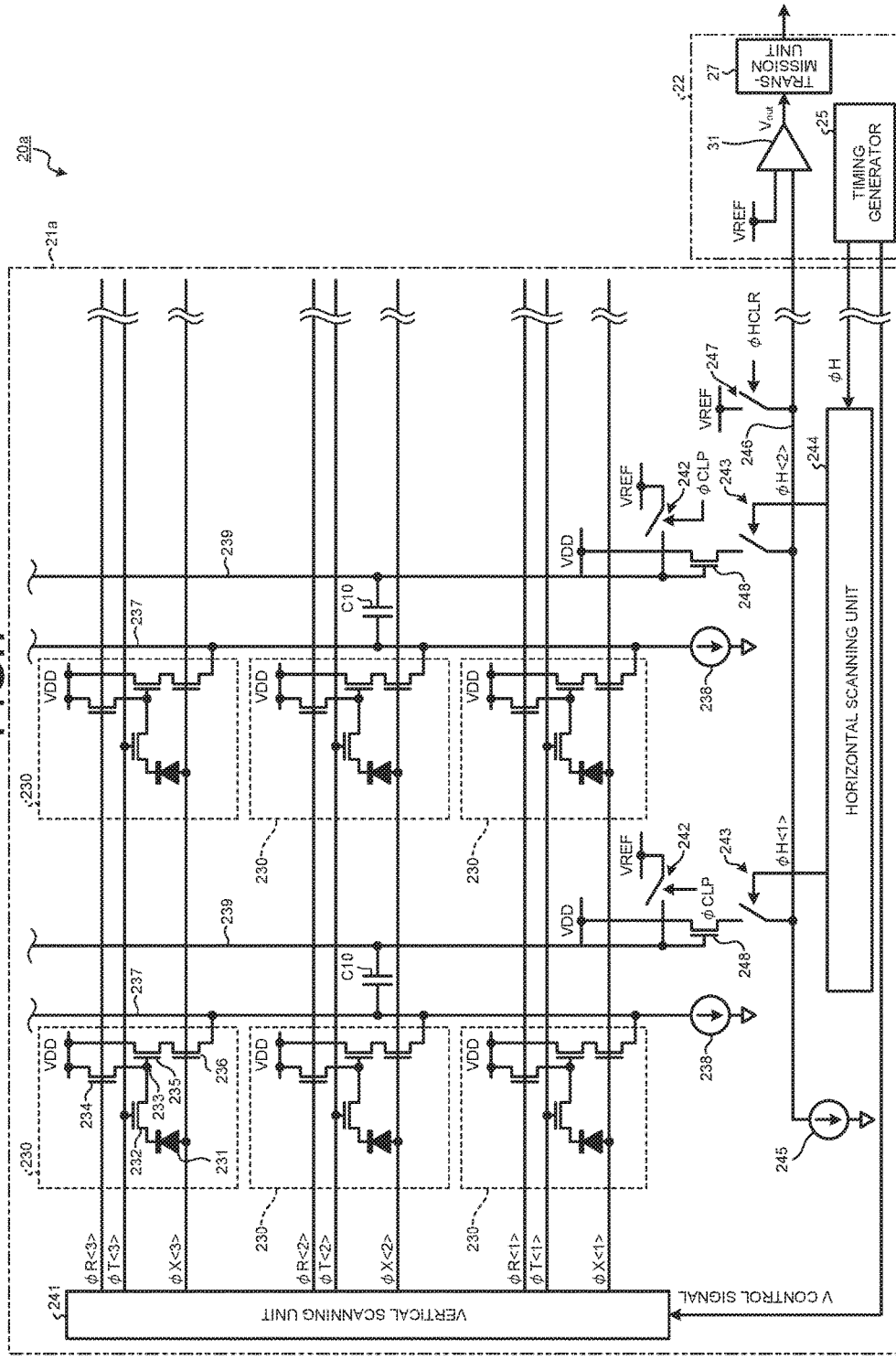
FIG. 7 is a block diagram illustrating a detailed configuration of an imaging unit according to a modification of the first embodiment of the present disclosure.

FIG. 7 is a block diagram illustrating a detailed configuration of an imaging unit according to the modification of the first embodiment. As illustrated in FIG. 7, an imaging unit 20a includes a first chip 21a and the second chip 22.

As illustrated in FIG. 7, in addition to the configuration of the first chip 21 according to the above-described first embodiment, the first chip 21a includes a buffer unit 248 and a constant current source 245 that allows the amplified signal to be output from the buffer unit 248. The buffer unit 248 amplifies an imaging signal transferred from the second transfer line 239 and outputs the amplified signal to the third transfer line 246. The buffer unit 248 has one end side connected to the power supply voltage VDD, the other end side being connected to the output switch 243, and has the gate connected to the second transfer line 239.

According to the modification of the first embodiment described above, the buffer unit 248 is provided between the second transfer line 239 and the output switch 243, making it possible to enhance the noise resistance of the imaging signal transferred from the second transfer line 239 and increase the S/N ratio.

Second Embodiment

Next, a second embodiment will be described. The second embodiment further includes a column AD converter in addition to the configuration of the imaging unit 20 according to the above-described first embodiment. Hereinafter, an imaging unit according to the second embodiment will be described. A same reference sign will be given to the configuration identical to the configuration of the endoscope system 1 according to the above-described first embodiment, and description therefor will be omitted.

Detailed Configuration of Imaging Unit

Figure 8:
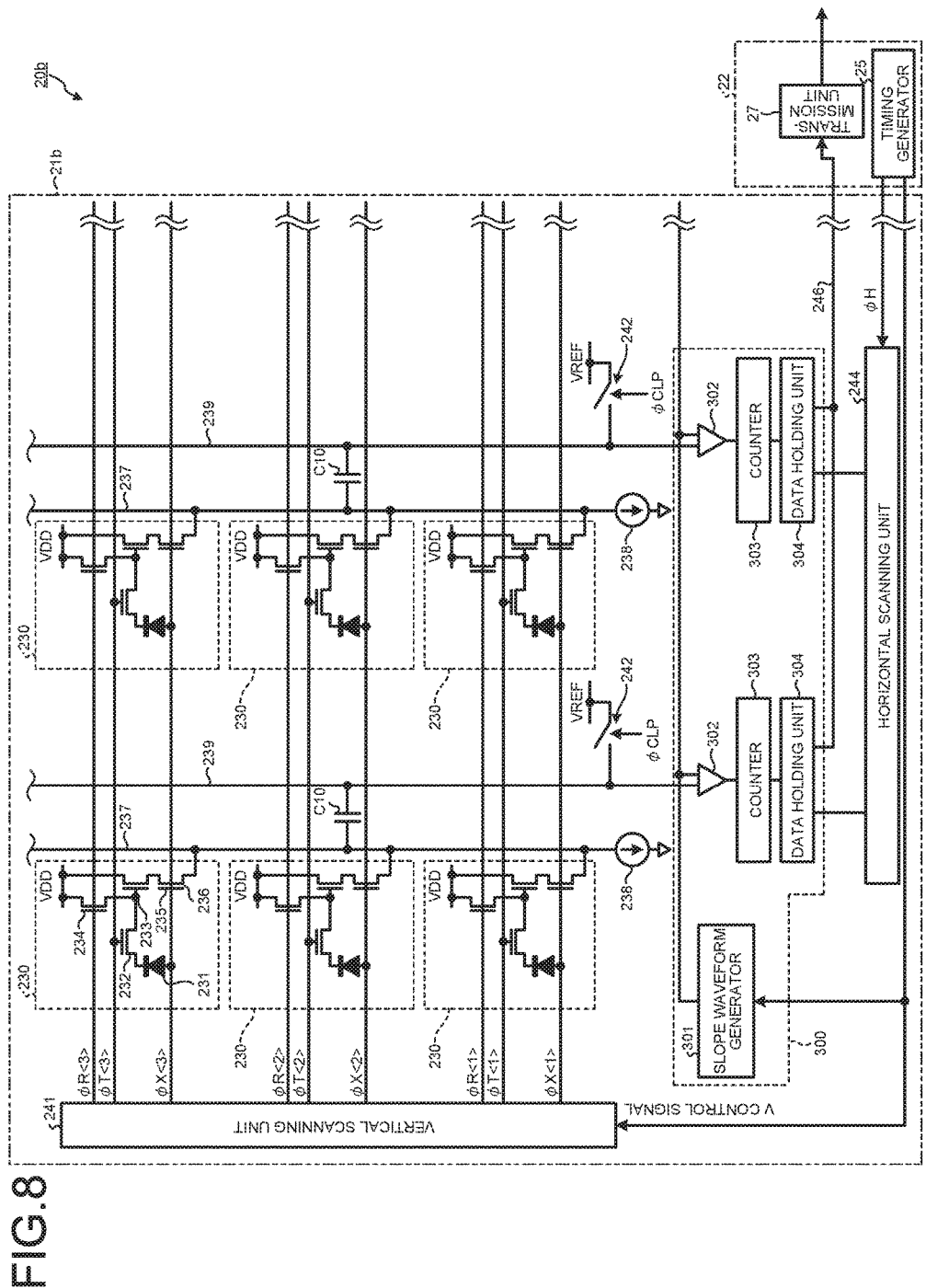
FIG. 8 is a block diagram illustrating a detailed configuration of an imaging unit according to a second embodiment of the present disclosure.

FIG. 8 is a block diagram illustrating a detailed configuration of an imaging unit according to the second embodiment. An imaging unit 20b illustrated in FIG. 8 includes a first chip 21b instead of the first chip 21 according to the above-described first embodiment. A reading unit of the first chip 21b includes a column AD converter 300 instead of the output switch 243 according to the above-described first embodiment. The column AD converter 300 converts an analog imaging signal transferred from the second transfer line 239 into a digital imaging signal and outputs the converted signal to the third transfer line 246.

The column AD converter 300 includes a slope waveform generator 301, a comparator 302, a counter 303, and a data holding unit 304. Note that the column AD converter 300 may be constituted with a latch circuit instead of the comparator 302 and the counter 303.

The slope waveform generator 301 generates a slope waveform and supplies the generated slope waveform to the comparator 302.

The comparator 302 compares the imaging signal supplied from the second transfer line 239 with the slope waveform supplied from the slope waveform generator 301 and outputs the result to the counter 303.

The data holding unit 304 holds the data of the counter 303, and outputs the held data to the third transfer line 246 in a case where the column selection pulse φH <N> supplied from the horizontal scanning unit 244 is input.

According to the second embodiment described above, the timing generator 25 causes the column AD converter 300 to operate and output the imaging signal converted into digital to the transmission unit 27 while allowing the unit pixel 230 to output the imaging signal. This makes it possible to enhance resistance to noise superimposed by the transmission cable 3 and to increase the S/N ratio.

Third Embodiment

Next, a third embodiment will be described. The third embodiment is different in configuration from the imaging unit 20 according to the above-described first embodiment. Specifically, in the third embodiment, a latter stage portion of the reading unit is formed on the second chip side. A same reference sign will be given to the configuration identical to the configuration of the endoscope system 1 according to the above-described first embodiment, and description therefor will be omitted.

Configuration of Imaging Unit

Figure 9:
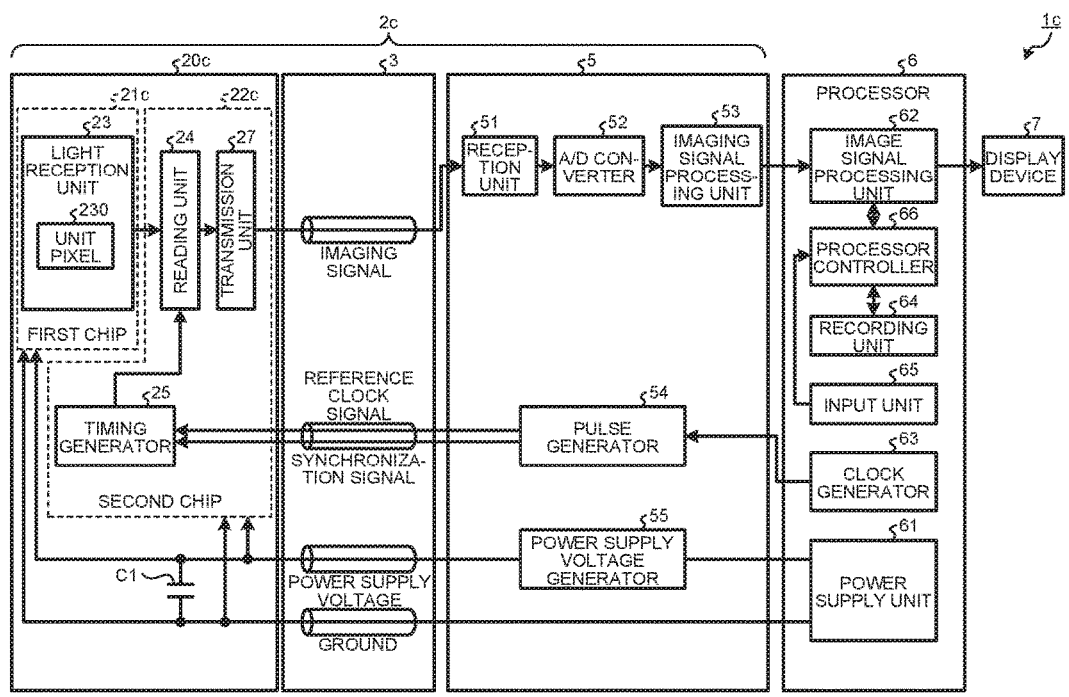
FIG. 9 is a block diagram illustrating a function of a main portion of an endoscope system according to a third embodiment of the present disclosure.

FIG. 9 is a block diagram illustrating a function of a main portion of an endoscope system according to the third embodiment. An endoscope system 1c illustrated in FIG. 9 includes an endoscope 2c instead of the endoscope 2 according to the above-described first embodiment. The endoscope 2c includes an imaging unit 20c instead of the imaging unit 20 of the endoscope 2 according to the above-described first embodiment. The imaging unit 20c includes a first chip 21c and a second chip 22c.

The first chip 21c is arranged in a two-dimensional matrix, and includes a light reception unit 23. The plurality of unit pixels 230 configured to receive light from the outside and generate and output an imaging signal corresponding to the amount of received light is arranged in the light reception unit 23. Details of the first chip 21c will be described below.

The second chip 22c includes the reading unit 24, a timing generator 25, and the transmission unit 27. The reading unit 24 reads an imaging signal photoelectrically converted by each of the plurality of unit pixels 230 in the light reception unit 23. The timing generator 25 generates a timing signal on the basis of a reference clock signal and a synchronization signal input from the connector unit 5 and outputs the generated timing signal to the reading unit 24. The transmission unit 27 amplifies the imaging signal output from the reading unit 24 and outputs the amplified signal to the transmission cable 3. Details of the second chip 22c will be described below.

Detailed Configuration of Imaging Unit

Figure 10:
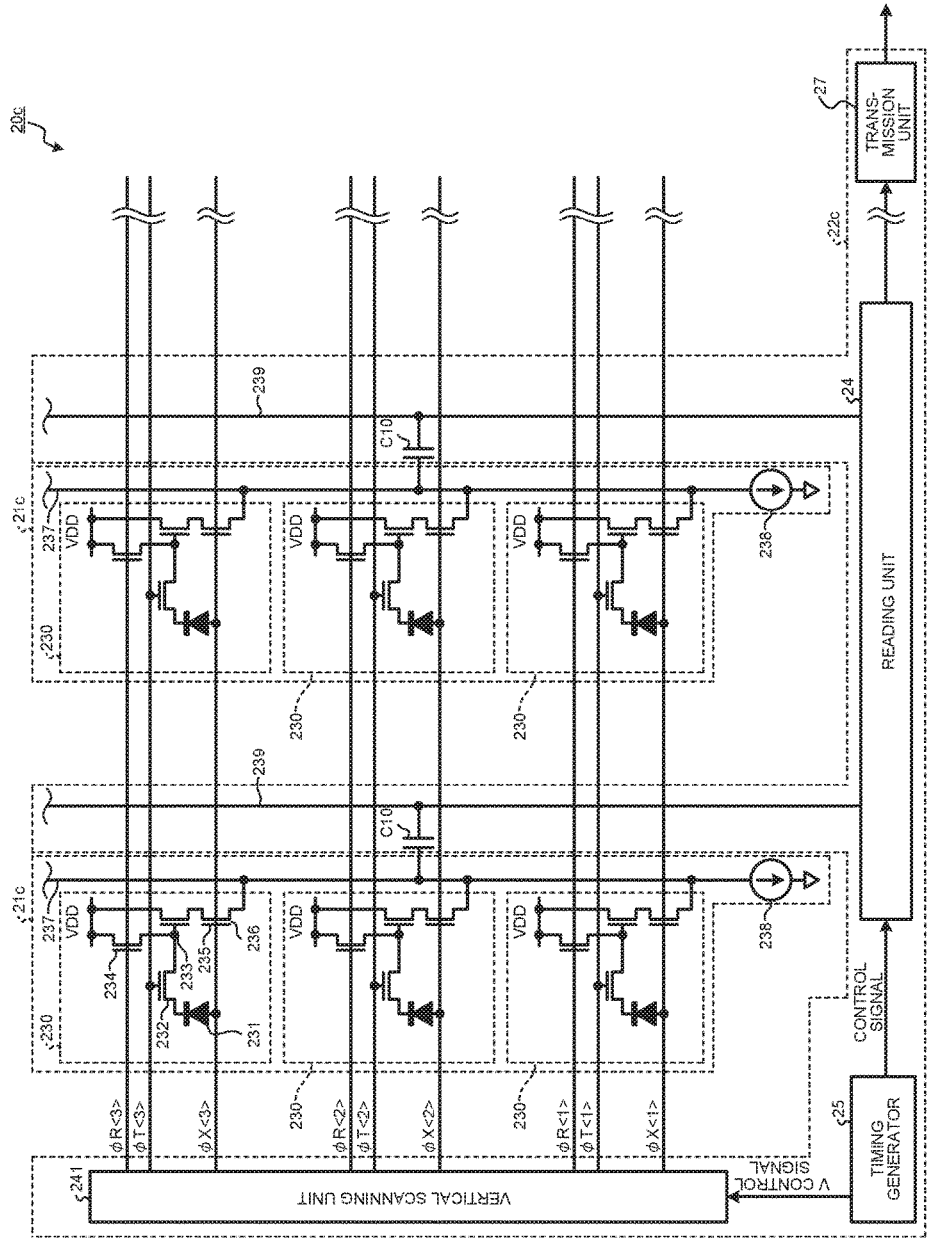
FIG. 10 is a block diagram illustrating a detailed configuration of an imaging unit illustrated in FIG. 9.

Next, detailed configurations of the first chip 21c and the second chip 22c in the above-described imaging unit 20c will be described. FIG. 10 is a block diagram illustrating the detailed configuration of the imaging unit 20c illustrated in FIG. 9.

Detailed Configuration of First Chip

First, a detailed configuration of the first chip 21c will be described.

As illustrated in FIG. 10, the first chip 21c includes the plurality of unit pixels 230 arranged in a two-dimensional matrix, the plurality of first transfer lines 237, and the constant current source 238 provided in each of the plurality of first transfer lines 237.

Detailed Configuration of the Second Chip

Next, a detailed configuration of the second chip 22c will be described.

As illustrated in FIG. 10, the second chip 22c includes the plurality of second transfer lines 239, the vertical scanning unit 241, the reading unit 24 that reads an imaging signal from each of the unit pixels 230, the timing generator 25, and the transmission unit 27.

In the imaging unit 20c configured as described above, the timing generator 25 causes the reading unit 24 to operate while allowing the unit pixel 230 to output the imaging signal.

Structure of Imaging Unit

Figure 11:
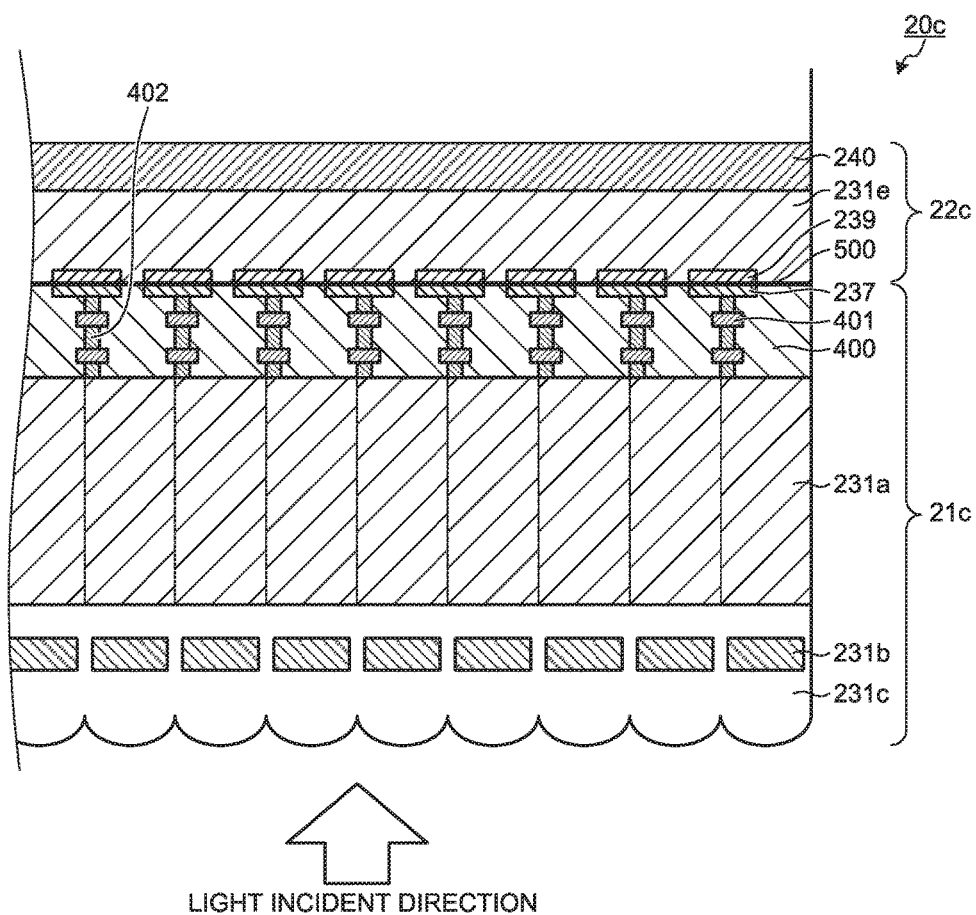
FIG. 11 is a diagram illustrating a cross-sectional structure of the imaging unit according to the third embodiment of the present disclosure.

Next, a structure of the imaging unit 20c will be described. FIG. 11 is a diagram illustrating a cross-sectional structure of the imaging unit 20c.

As illustrated in FIG. 11, the first chip 21c is formed by stacking the on-chip color filter 231b and the on-chip microlens 231c in this order on the front surface side (light incident direction) of the silicon substrate 231a (light reception unit). Moreover, the first chip 21c is formed by stacking an interlayer insulating film 400 and the first transfer line 237 in this order on the back surface side of the silicon substrate 231a. Moreover, the first transfer line 237 is connected to the source region of the pixel output switch 236 formed on the silicon substrate 231a via the interlayer insulating film 400 by metal wiring 401, a via hole 402, or the like. Furthermore, the dielectric 500 is stacked on the back surface of the first transfer line 237.

The second chip 22c is formed by stacking the interlayer insulating film 231e and the second transfer line 239 in this order on the front surface side (light incidence direction) of a silicon substrate 240 on which the reading unit 24 is formed.

Furthermore, the imaging unit 20c is formed by stacking the first transfer line 237 formed on the back surface of the first chip 21c being arranged as a first electrode and the second transfer line 239 as a second electrode being arranged at the position opposing the first transfer line 237, via the dielectric 500. Moreover, the first transfer line 237 and the second transfer line 239 formed in pairs are arranged in parallel along the stacking direction of the first chip 21c and the second chip 22c. With this configuration, it is possible to enable the imaging unit 20c to have the capacitance C10 (column capacitance) formed by the plurality of first transfer lines 237 and the plurality of second transfer lines 239 each corresponding to each of the plurality of first transfer lines 237 in pairs, without a need to separately provide a column capacity in the first chip 21c.

The imaging unit 20c includes the timing generator 25, the reading unit 24 (for example, the vertical scanning unit 241, the clamp unit 242, the output switch 243, the horizontal scanning unit 244, the third transfer line 246, the horizontal reset unit 247, and the output unit 31, in FIG. 3), and the second transfer line 239, formed on the front surface side (light incident direction) of the silicon substrate 240 of the second chip 22c. With this configuration, by forming a capacitor and stacking the capacitance C10 (capacitor) with the first chip 21c instead of a through silicon via (TSV) consuming an active region of the silicon substrate 240 at the time of chip stacking, it is possible to enhance the area efficiency and thus, to further miniaturize the imaging unit 20c.

According to the third embodiment described above, the first transfer line 237 formed on the back surface of the first chip 21c is used as the first electrode, and the second transfer line 239 is arranged as the second electrode at the position facing the first transfer line 237, via the dielectric 500, to be stacked so as to form the capacitance C10 (column capacitance) by the plurality of first transfer line 237 and the plurality of second transfer line 239 corresponding to each of the plurality of first transfer line 237 in pairs. With this arrangement, it is possible to completely eliminate the column circuit area and the column TSV area from the first chip 21c including the light reception unit 23, and thus, to further miniaturize the imaging unit 20c.

Modification of Third Embodiment

Next, a modification of the third embodiment will be described. The modification of the third embodiment is different in the configuration of the first chip. Specifically, in the modification of the third embodiment, the above-described vertical scanning unit is arranged on the first chip. Hereinafter, a configuration of the first chip of the imaging unit according to the modification of the third embodiment will be described. A same reference sign will be given to the configuration identical to the configuration of the above-described third embodiment, and description thereof will be omitted.

Figure 12:
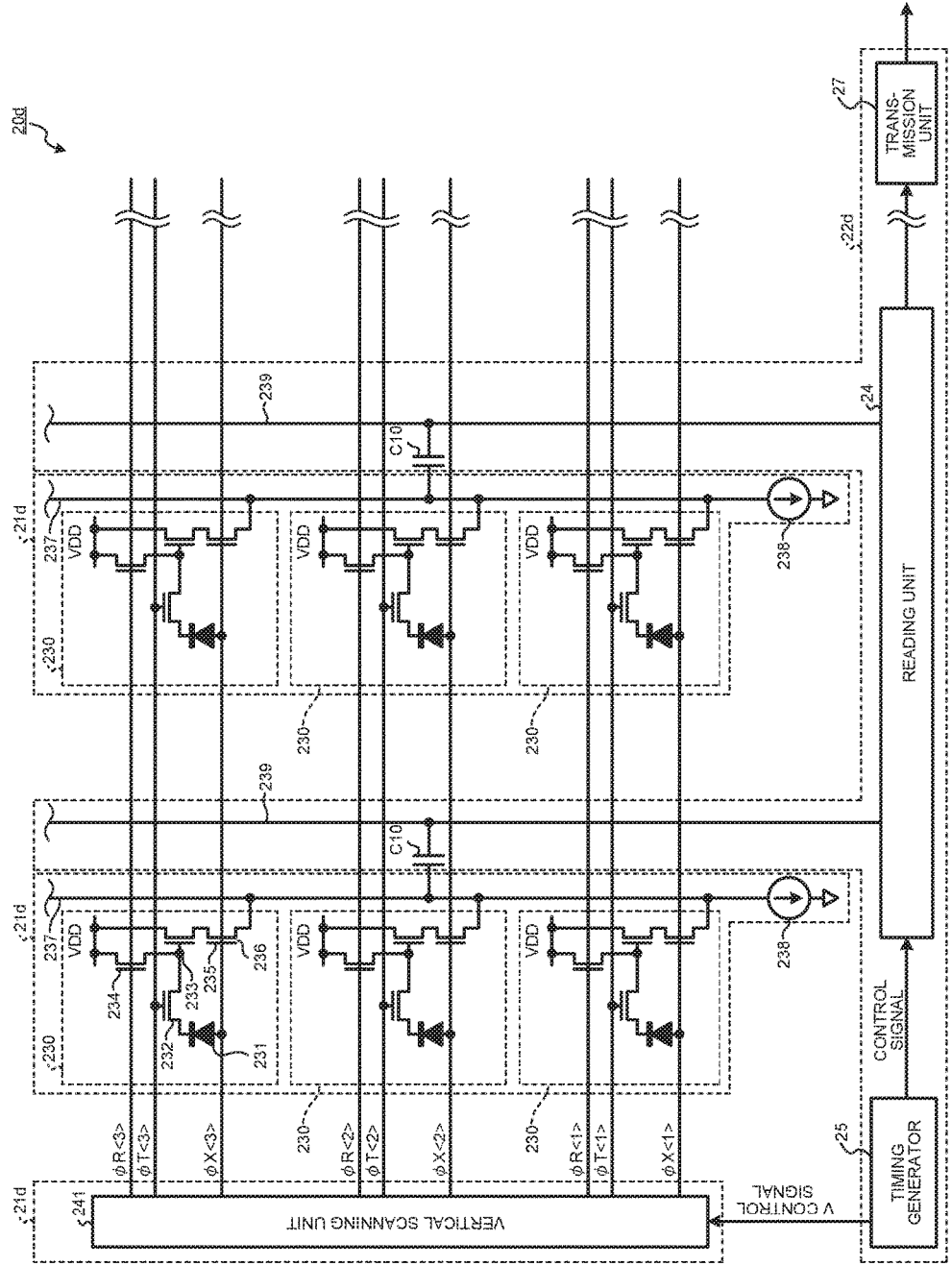
FIG. 12 is a diagram illustrating a cross-sectional structure of an imaging unit according to a modification of the third embodiment of the present disclosure.

FIG. 12 is a block diagram illustrating a detailed configuration of an imaging unit according to the modification of the third embodiment. An imaging unit 20d illustrated in FIG. 12 includes a first chip 21d and a second chip 22d.

Detailed Configuration of First Chip

First, a detailed configuration of the first chip 21d will be described.

As illustrated in FIG. 12, the first chip 21d further includes the vertical scanning unit 241 in addition to the configuration of the first chip 21c of the above-described third embodiment.

Detailed Configuration of the Second Chip

Next, a detailed configuration of the second chip 22d will be described.

As illustrated in FIG. 12, the second chip 22d is obtained by eliminating the vertical scanning unit 241 from the configuration of the second chip 22c of the above-described third embodiment.

According to the modification of the third embodiment described above, there is no need to arrange pixel drive wiring for each of the rows as compared with the above-described third embodiment. This configuration may reduce the number of TSV consuming the active region, making it possible to achieve further miniaturization.

Other Embodiments

While the present embodiment describes a case of the endoscope to be inserted into the subject, the present disclosure may also be applied to a capsule endoscope or an imaging apparatus that images a subject, for example. In particular, the present disclosure may be applied to an apparatus using an image sensor having a small number of pixels.

In the timing charts in this description, context of the processing is described by using expressions such as "first", "thereafter", and "subsequently", but the sequences of the processing needed for implementing the present disclosure are not intended to be uniquely defined by these expressions. In other words, the order of processing in the timing charts described herein may be changed within a range implementable without contradiction.

In this manner, the present disclosure in its broader aspects is not limited to the representative embodiments described herein. Accordingly, various modifications may be made without departing from the spirit or scope of the general inventive concept as defined by the appended claims and their equivalents.

According to the present disclosure, it is possible to achieve an effect of achieving further miniaturization.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image sensor comprising:
   a light reception unit arranged in a two-dimensional matrix and including a plurality of pixels configured to receive light from an outside and generate imaging signals corresponding to an amount of the received light;
   a plurality of first transfer lines arranged on a back surface of a light receiving surface of the light reception unit and each configured to transfer the imaging signals;
   a constant current source provided in each of the plurality of first transfer lines and configured to output the imaging signals from the pixel to the first transfer line;
   a plurality of second transfer lines each configured to form a capacitance in pairs with one of the plurality of first transfer lines and individually transfer the imaging signals output by the first transfer line;

a controller configured to cause the imaging signals transferred by the plurality of second transfer lines to be read while the pixel is outputting the imaging signals;

a dielectric interposed between the first and second transfer lines formed in pairs;

a first chip including at least the light reception unit, the plurality of first transfer lines, and the constant current source, each being mounted on the first chip; and a second chip including at least the plurality of second transfer lines mounted on the second chip, wherein the first chip is configured such that the second chip is stacked on the back surface of the light receiving surface, and each of the plurality of second transfer lines is arranged at a position facing one of the plurality of first transfer lines with the dielectric interposed between the first and second transfer lines.

2. The image sensor according to claim 1, wherein the capacitance formed by each of the first and second transfer lines is substantially equal for each pair of first and second transfer lines.

3. The image sensor according to claim 1, wherein
the first and second transfer lines are formed with metal wirings, and
the capacitance between the first and second transfer lines formed in pairs is formed by arranging the dielectric between the metal wirings constituting the respective transfer lines.

4. An endoscope comprising the image sensor according to claim 1 provided on a distal end side of an insertion unit insertable into a subject.

5. An endoscope system comprising:
the endoscope according to claim 4; and
an image processing apparatus configured to convert the imaging signals into image signals.

6. The image sensor according to claim 1, wherein
the first chip and the second chip are layered;
the dielectric forms capacitive coupling between each of the first transfer lines on the first chip and a respective one of the second transfer lines on the second chip to simultaneously perform an interlayer connection between the first chip and the second chip; and
the imaging signal transferred by each of the first transfer lines on the first chip is transferred by the respective one of the second transfer lines on the second chip.

* * * * *